United States Patent
Watanabe et al.

(10) Patent No.: US 9,308,159 B2
(45) Date of Patent: Apr. 12, 2016

(54) OIL-IN-WATER EMULSION COMPOSITION

(71) Applicant: SHISEIDO COMPANY, LTD., Tokyo (JP)

(72) Inventors: Takumi Watanabe, Yokohama (JP); Takayuki Omura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/364,919

(22) PCT Filed: Nov. 30, 2012

(86) PCT No.: PCT/JP2012/081044
§ 371 (c)(1),
(2) Date: Aug. 13, 2014

(87) PCT Pub. No.: WO2013/094384
PCT Pub. Date: Jun. 27, 2013

(65) Prior Publication Data
US 2015/0005396 A1    Jan. 1, 2015

(30) Foreign Application Priority Data
Dec. 19, 2011    (JP) .................. 2011-277274

(51) Int. Cl.
| | | |
|---|---|---|
| A61K 8/895 | (2006.01) | |
| A61K 8/06 | (2006.01) | |
| A61Q 19/00 | (2006.01) | |
| A61K 8/891 | (2006.01) | |
| A61K 8/894 | (2006.01) | |
| A61K 8/86 | (2006.01) | |
| A61K 8/89 | (2006.01) | |
| A61Q 19/08 | (2006.01) | |
| A61K 8/87 | (2006.01) | |

(52) U.S. Cl.
CPC ............. *A61K 8/895* (2013.01); *A61K 8/062* (2013.01); *A61K 8/86* (2013.01); *A61K 8/87* (2013.01); *A61K 8/89* (2013.01); *A61K 8/891* (2013.01); *A61K 8/894* (2013.01); *A61Q 19/00* (2013.01); *A61Q 19/005* (2013.01); *A61Q 19/08* (2013.01); *A61K 2800/48* (2013.01); *A61K 2800/548* (2013.01); *A61K 2800/594* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 2008/0181956 A1* | 7/2008 | Ha et al. .......... | 424/489 |
| 2012/0045403 A1* | 2/2012 | Ikebe et al. ....... | 424/59 |
| 2013/0156831 A1* | 6/2013 | Matsuo et al. ...... | 424/401 |

FOREIGN PATENT DOCUMENTS

| | | |
|---|---|---|
| DE | 10 2006 040 903 | 3/2008 |
| DE | 10 2010 028 313 | 11/2011 |
| EP | 1 013 264 | 6/2000 |
| EP | 2 450 029 | 5/2012 |
| JP | 2005-68023 | 3/2005 |
| JP | 2009-517478 | 4/2009 |
| JP | A-2009-540056 | 11/2009 |
| JP | 2009286723 | 12/2009 |
| JP | 2010-95466 | 4/2010 |
| JP | A-2013-126963 | 6/2013 |
| JP | B-5373046 | 12/2013 |
| WO | WO 2011/001633 | 1/2011 |
| WO | WO 2011/158679 | 12/2011 |

OTHER PUBLICATIONS

Notice of Reasons for Rejection dated Feb. 22, 2013, 2 pages—English; 2 pages—Japanese.
Written Argument dated Apr. 10, 2013, 2 pages—English; 2 pages—Japanese.
Written Amendment dated Apr. 10, 2013, 2 pages—English; 1 page—Japanese.
JPO Decision to Grant dated Sep. 6, 2013, 3 pages—English; 3 pages—Japanese.
Granted Claims, 2 pages—English; and certificate of translation.
List of Documents issued from and filed to the JPO in the Examination of JP2011-277274.
PCT/JP2012/081044 International Search Report, mailed Mar. 5, 2013, 2 pages—English; 2 pages—Japanese.
EP 12859445.4 European Search Report dated Jun. 30, 2015, 7 pages—English.
Cosmetic Composition for Optical Lamination of Wrinkles, Bialasinski, Stadler, Waldmann-Laue, 9 pages—English, http://www.google.com/patents/DE102010028313A1?cl=en, dated Nov. 10, 2015, IFI Claims Patent Services.
Cosmetic composition for non-therapeutic skin treatment, e.g. antiwrinkle cream, contains silicone elastomer in aqueous dispersion, silicone elastomer in silicone-based gel, plus aqueous and oil phases, Frisoli, Struwe, Weldmann-Laue, 26 pages—English, dated Nov. 10, 2015, IFI Claims Patent Services.

* cited by examiner

*Primary Examiner* — Tigabu Kassa
(74) *Attorney, Agent, or Firm* — Andrew F. Young, Esq.; Lackenbach Siegel LLP

(57) ABSTRACT

Provided is an oil-in-water emulsion composition which, while having a fresh feel without stickiness when used, has a skin unevenness correction effect and persistence thereof, and provides excellent smoothness, moisture and shininess, and feeling of tension. The oil-in-water emulsion composition is characterized by containing, in a specific ratio: (A) a non-emulsifying cross-linked polymethyl siloxane, which contains (a1) a dimethicone crosspolymer and (a2) a non-emulsifying cross-linked polymethyl siloxane other than a dimethicone crosspolymer; (B) an associative thickener; (C) a polyether-modified silicone; (D) a silicone oil; and (E) water in a specific ratio. The oil-in-water emulsion composition is further characterized in that the mass ratio ((a2)/(a1)) of (a2) the non-emulsifying cross-linked polymethyl siloxane other than a dimethicone crosspolymer to (a1) the dimethicone crosspolymer falls within a range of 0.1 to 2.5.

9 Claims, No Drawings

OIL-IN-WATER EMULSION COMPOSITION

CROSS REFERENCE TO RELATED APPLICATIONS

This application claims priority to International Ser. No. PCT/JP2012/081044 filed Nov. 30, 2012, the entire contents of which are incorporated herein fully by reference, which in turn claims priority to JP Ser. No. JP 2011-277274 filed on Dec. 19, 2011.

TECHNICAL FIELD

The present invention relates to an oil-in-water emulsion composition providing watery and non-sticky feeling upon use and imparting excellent skin roughness-covering effect and its persistency, firmness/elasticity, smoothness, moist feeling and shiny appearance to the skin.

BACKGROUND ART

Up to the present, making the skin pretty and helping makeup last longer have been carried out by smoothening irregularities in the skin due to e.g. pores and fine wrinkles.

As the skin cosmetics for use in such treatment, for example, aqueous gel cosmetics containing a silica-coated silicone elastomer and an associative thickening agent have been proposed (Patent document 1). The cosmetics have a roughness-covering effect and can be overlaid on a foundation as well as imparting firmness/elasticity to the skin. However, the aqueous gel cosmetics contain no oil contents. Because of this, sense of use including moist feeling and shiny appearance is unsatisfactory and persistency of roughness-covering effect tends to be inferior. Furthermore, since the cosmetics are developed for the purpose of overlaying on a foundation, formulation ingredients and contents are limited, and it is difficult to obtain satisfactory roughness-covering effect and sense of use (firmness/elasticity, smoothness, moist feeling, and shiny appearance).

PRIOR ART

Patent Document

Patent document 1: Japanese Patent Laid-Open No. 2009-286723

SUMMARY OF INVENTION

Technical Problem

The present invention was made in consideration of drawbacks in the related art and is directed to provide an oil-in-water emulsion composition providing watery and non-sticky feeling upon use and imparting excellent skin roughness-covering effect and its persistency, firmness/elasticity, smoothness, moist feeling and shiny appearance to the skin.

Solution to Problem

The present inventors conducted intensive studies and found that a cosmetic, which imparts a high roughness-covering effect and its persistency and excellent sense of use including firmness/elasticity, smoothness, moist feeling and shiny appearance to the skin can be obtained by preparing an oil-in-water emulsion composition so as to contain two types of non-emulsifying crosslinked polymethylsiloxanes, an associative thickening agent, a polyether-modified silicone, a silicone oil and water in a predetermined blending ratio. Based on the finding, they accomplished the present invention.

More specifically, the summary of the present invention is as follows.

(1) An oil-in-water emulsion composition comprising
(A) 0.5 to 5.0 mass % of a non-emulsifying crosslinked polymethylsiloxane comprising the following components (a1) and (a2):
(a1) a dimethicone cross polymer, and
(a2) a non-emulsifying crosslinked polymethylsiloxane except the dimethicone cross polymer,
(B) 0.5 to 5.0 mass % of an associative thickening agent,
(C) 0.5 to 5.0 mass % of a polyether-modified silicone,
(D) a silicone oil, and
(E) water,
wherein
the mass ratio ((a2)/(a1)) of the non-emulsifying crosslinked polymethylsiloxane (a2) except the dimethicone cross polymer relative to the dimethicone cross polymer (a1) falls within the range of 0.1 to 2.5.

(2) The oil-in-water emulsion composition according to (1), wherein the mass ratio ((a2)/(a1)) of the non-emulsifying crosslinked polymethylsiloxane (a2) except the dimethicone cross polymer relative to the dimethicone cross polymer (a1) falls within the range of 0.1 to 1.5.

(3) The oil-in-water emulsion composition according to (1) or (2), wherein the non-emulsifying crosslinked polymethylsiloxane (a2) except the dimethicone cross polymer is one or two or more selected from the group consisting of a dimethicone/vinyldimethicone cross polymer, a dimethicone/phenylvinyldimethicone cross polymer and a vinyldimethicone/lauryldimethicone cross polymer.

(4) The oil-in-water emulsion composition according to any one of (1) to (3), wherein the content of the silicone oil is 3.0 to 30 mass % in the entire composition.

Advantageous Effects of Invention

According to the present invention, the oil-in-water emulsion composition not only provides watery and non-sticky feeling upon use but also imparts excellent sense of use including skin roughness-covering effect and its persistency, firmness/elasticity, smoothness, moist feeling and shiny appearance to the skin.

DETAILED DESCRIPTION

The oil-in-water emulsion composition of the present invention is characterized by comprising (A) a non-emulsifying crosslinked polymethylsiloxane comprising (a1) a dimethicone cross polymer and (a2) a non-emulsifying crosslinked polymethylsiloxane except the dimethicone cross polymer, (B) an associative thickening agent, (C) a polyether-modified silicone, (D) a silicone oil and (E) water in a predetermined ratio. Now, the present invention will be more specifically described below.

<(A) Non-Emulsifying Crosslinked Polymethylsiloxane>

The non-emulsifying crosslinked polymethylsiloxane (A) to be used in the present invention is a combination of at least two types of components, i.e., (a1) a dimethicone cross polymer and (a2) a non-emulsifying crosslinked polymethylsiloxane except the dimethicone cross polymer.

(a1) Dimethicone Cross Polymer

The dimethicone cross polymer (a1) to be used in the present invention refers to a dimethicone cross polymer (the INCI nomenclature) obtained by a crosslinking reaction between an organohydrogensiloxane and an alkene.

The dimethicone cross polymer (a1) is preferably blended in a swollen state with a low-viscosity oil, particularly, a linear or cyclic silicone oil. Examples of commercially available dimethicone cross polymers in a swollen state include products available from Dow Corning Toray Co., Ltd., such as "DC9040" (trade name) which is a mixture of a dimethicone cross polymer and decamethylcyclopentasiloxane (the actual quantity of the cross polymer: 12%), "DC9041" (trade name) which is a mixture of a dimethicone cross polymer and dimethicone mPa·s (the actual quantity of the cross polymer: 16%), and "DC9045" (trade name) which is a mixture of a dimethicone cross polymer and a decamethylcyclopentasiloxane (the actual quantity of the cross polymer: 12.5%). Of them, "DC9041" (trade name) is particularly preferred since it provides excellent roughness-covering effect immediately after application and provides excellent feeling upon use, i.e., less sticky, smooth and silky feeling.

(a2) Non-Emulsifying Crosslinked Polymethylsiloxane Except the Dimethicone Cross Polymer The non-emulsifying crosslinked polymethylsiloxane (a2) except the dimethicone cross polymer to be used in the present invention refers to one or two or more selected from the group consisting of a dimethicone/vinyldimethicone cross polymer (INCI nomenclature), which is obtained by a crosslinking reaction between an organohydrogensiloxane and vinyldimethylsiloxane; a dimethicone/phenylvinyldimethicone cross polymer (INCI nomenclature) (also called "polysilicone-11"), which is obtained by a crosslinking reaction between an organohydrogensiloxane and phenylvinyldimethylsiloxane; and a vinyldimethicone/lauryldimethicone cross polymer (INCI nomenclature), which is obtained by a crosslinking reaction between a laurylorganohydrogensiloxane and vinyldimethylsiloxane.

The non-emulsifying crosslinked polymethylsiloxane (a2) except the dimethicone cross polymer is preferably blended in a swollen state with a low viscosity oil, particularly, a linear or cyclic silicone oil. Examples of such a swollen product include commercially available products from Shin-Etsu Chemical Co., Ltd., such as "KSG-15" (trade name), which is a mixture of a dimethicone/vinyldimethicone cross polymer and a cyclopentasiloxane (actual quantity: about 5%), "KSG-16" (trade name), which is a mixture of a dimethicone/vinyldimethicone cross polymer and dimethicone 6 mPa·s (actual quantity: about 25%), "KSG-18" (trade name), which is a mixture of a dimethicone/phenylvinyldimethicone cross polymer and phenyltrimethicone (actual quantity: about 15%), "KSG-41" (trade name), which is a mixture of a vinyldimethicone/lauryldimethicone cross polymer and liquid paraffin (actual quantity: about 30%), "KSG-42" (trade name), which is a mixture of a vinyldimethicone/lauryldimethicone cross polymer and light isoparaffin (actual quantity: about 25%), "KSG-43" (trade name), which is a mixture of a vinyldimethicone/lauryldimethicone cross polymer and glyceryl tri(2-ethylhexanoate) (actual quantity: about 30%), and "KSG-44" (trade name), which is a mixture of a vinyldimethicone/lauryldimethicone cross polymer and squalane (actual quantity: about 5%); and commercially available products from GRANT such as "GRANSIL GCM" (trade name), which is a mixture of polysilicone-11 and octamethylcyclotetrasiloxane (actual quantity: about 6%), "GRANSIL GCM-5" (trade name), which is a mixture of polysilicone-11 and decamethylcyclopentasiloxane (actual quantity: about 6%), "GRANSIL IDS" (trade name), which is a mixture of polysilicone-11 and isodecane (actual quantity: about 7%), "GRANSIL DMG-6" (trade name), which is a mixture of polysilicone-11 and dimethicone 6 mPa·s (actual quantity: about 18%), "GRANSIL DMG-20" (trade name), which is a mixture of polysilicone-11 and dimethicone 20 mPa·s (actual quantity: about 25%), "GRANSIL DMG-50" (trade name), which is a mixture of polysilicone-11 and dimethicone 50 mPa·s (actual quantity: about 26%), "GRANSIL PM" (trade name), which is a mixture of polysilicone-11 and phenyltrimethicone (actual quantity: about 20%), and "GRANSIL ININ" (trade name), which is a mixture of polysilicone-11 and isononyl isononanoate (actual quantity: about 15%). Of them "KSG-18" (trade name) is particularly preferred since it has excellent persistency of a roughness-covering effect and provides excellent moist feeling and shiny appearance.

Mass Ratio of (a1) and (a2)

The mass ratio ((a2)/(a1)), which is a mass ratio of the non-emulsifying crosslinked polymethylsiloxane (a2) except the dimethicone cross polymer relative to the dimethicone cross polymer (a1), falls within the range of 0.1 to 2.5, preferably 0.1 to 1.5 and further preferably 0.2 to 1.0. The mass ratio herein refers to the mass ratio of actual contents of crosslinked polymers. If the mass ratio is less than 0.1, persistency of a roughness-covering effect, moist feeling and shiny appearance after application cannot be sufficiently obtained. In contrast, if the mass ratio exceeds 2.5, the roughness-covering effect and smoothness immediately after application cannot be sufficiently obtained.

Content of (A) Non-Emulsifying Crosslinked Polymethylsiloxane

The content of non-emulsifying crosslinked polymethylsiloxane (A) (total of actual contents of (a1) and (a2)) is 0.5 to 5.0 mass %, preferably 1.0 to 3.0 mass % and further preferably 1.5 to 2.5 mass % relative to the total amount of the oil-in-water emulsion composition. If the content is less than 0.5 mass %, the roughness-covering effect is not sufficiently obtained and smoothness, moist feeling and shiny appearance after application are not sufficiently obtained, either. In contrast, if the content exceeds 5.0 mass %, the roughness-covering effect is not enhanced and the resultant composition becomes sticky. Because of this, sense of use tends to be damaged.

<(B) Associative Thickening Agent>

The associative thickening agent (B) to be used in the present invention is a hydrophobically modified polyether urethane represented by the following general formula:

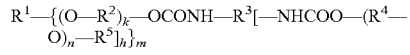

$$R^1-\{(O-R^2)_k-OCONH-R^3[-NHCOO-(R^4-O)_n-R^5]_h\}_m$$

wherein $R^1$, $R^2$ and $R^4$ may be the same or different and represent a hydrocarbon group; $R^3$ represents a hydrocarbon group that may have a urethane bond; $R^5$ represents a linear or branched divalent hydrocarbon group; m is an integer of 2 or more; h is an integer of 1 or more; and k and n are each independently an integer of 0 to 1000.

Association network is established by blending an associative thickening agent to enhance the viscosity of an aqueous system.

Examples of commercially available products of the hydrophobically modified polyether urethane include products from ADEKA Corporation such as "ADEKA NOL GT-700" (trade name) (PEG-240/decyltetradeceth-20/hexamethyldiisocyanate copolymer).

The associative thickening agent (B) is blended in an amount of 0.5 to 5.0 mass %, preferably 1.0 to 3.0 mass % and further preferably 1.2 to 2.0 mass % relative to the total amount of the oil-in-water emulsion composition. If the content is less than 0.5 mass %, a sufficient viscosity cannot be obtained and firmness/elasticity deteriorates. In contrast, if the content exceeds 5.0 mass %, viscosity increases, the resultant composition becomes sticky. Because of this, sense of use tends to be damaged.

<(C) Polyether-Modified Silicone>

The polyether-modified silicone (C) to be used in the present invention is a compound represented by the following general formula (1):

[Formula 1]

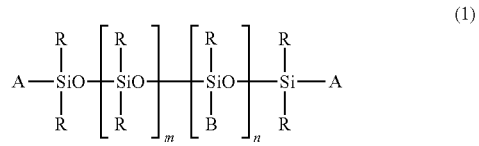

(1)

wherein A represents an alkyl group having 1 to 6 carbon atoms, a phenyl group or B (described later); B is a polyoxyalkylene group represented by the general formula: $-C_3H_6O(C_2H_4O)_a(C_3H_6O)_bR'$ where R' is a group selected from the group consisting of a hydrogen atom, an acyl group and an alkyl group having 1 to 6 carbon atoms; a is an integer of 0 to 50, b is an integer of 0 to 50, with the proviso that a and b are not simultaneously 0; R is each independently an alkyl group having 1 to 6 carbon atoms or a phenyl group; m is an integer of 50 to 1000, and n is an integer of 0 to 50, with the proviso that at least one polyoxyalkylene group is present in a molecule. In the above, n is preferably at least 1 and R preferably represents a methyl group.

Particularly preferable examples of the polyether-modified silicone (C) to be used in the present invention include commercially available products from Shin-Etsu Chemical Co., Ltd. such as "KF-6017" (trade name) and "KF-6028" (trade name).

The polyether-modified silicone (C) is blended in an amount of 0.5 to 5.0 mass %, preferably 0.5 to 3.0 mass % and further preferably 0.5 to 1.5 mass % relative to the total amount of the oil-in-water emulsion composition. If the content is less than 0.5 mass %, dispersibility and aggregation inhibition of the non-emulsifying crosslinked polymethylsiloxane (A) sometimes become insufficient. In contrast, if the content exceeds 5.0 mass %, the resultant composition becomes sticky. Because of this, sense of use tends to be damaged.

<(D) Silicone Oil>

The silicone oil (D) to be used in the present invention can be selected from a wide range of silicon oils generally used in cosmetics and put in use. Specific examples thereof include, but not limited to, linear or cyclic silicones such as methylpolysiloxane, octamethylsiloxane, decamethyltetrasiloxane, methylhydrogenpolysiloxane, methylphenyl polysiloxane, hexamethylcyclotrisiloxane, octamethylcyclotetrasiloxane and decamethyl cyclopentasiloxane. These can be used alone or in combination with two or more.

The silicone oil (D) is blended in an amount of 3.0 to 30 mass %, preferably 5.0 to 30 mass % and further preferably 10 to 25 mass % relative to the total amount of the oil-in-water emulsion composition. If the content is less than 3.0 mass %, dispersion of the non-emulsifying crosslinked polymethylsiloxane (A) sometimes becomes insufficient. In contrast, if the content exceeds 30 mass %, sense of use and stability of a preparation tend to be damaged.

<(E) Water>

The water (E) to be used in the present invention may be distilled water, ion-exchanged water or purified water. The water (E) is blended sufficiently enough to allow the total amount of the oil-in-water emulsion composition to reach 100%.

The oil-in-water emulsion composition according to the present invention, if necessary, may appropriately contain various types of components that are usually contained in cosmetics and quasi-drugs, as long as the effect of the present invention is not damaged. Examples of the components include a powder component, a solid fat and oil, a moisturizer, a thickening agent, a sequestering agent, a pigment, a pH moderator, a skin nutritional supplement, vitamins, an antiseptic, an antioxidant, an antioxidation aid and a fragrance.

Particularly, as the thickening agent, a water-soluble thickening agent can be blended other than the above associative thickening agent (B). Examples of the water-soluble thickening agent include plant-derived polymers such as Arabian gum, gum tragacanth, galactan, guar gum, carrageenan, pectin, a Quince Seed (*PYRUS CYDONIA* SEED) extract and brown alga powder; microbe-derived polymers such as xanthan gum, dextran, pullulan and succinoglycan; animal-derived polymers such as collagen, casein, albumin and gelatin; starches such as carboxymethyl starch and methylhydroxy starch; celluloses such as methylcellulose, nitrocellulose, ethylcellulose, methylhydroxypropylcellulose, hydroxyethylcellulose, cellulose sulfate, hydroxypropylcellulose, carboxymethylcellulose, crystalline cellulose and cellulose powder; vinyl polymers such as polyvinyl alcohol, polyvinyl methyl ether, polyvinylpyrrolidone and a carboxyvinyl polymer; and acrylic polymers such as a polyacrylic acid and a salt thereof, a polyacrylic imide and a dimethylacrylamide/sodium acryloyldimethyl taurine cross polymer. Other than these, e.g. glycyrrhizinic acid, alginic acid and a salt thereof are included. In addition, inorganic thickening agents such as bentonite, laponite, hectorite, magnesium aluminum silicate and silicic anhydride can be used.

The oil-in-water emulsion composition according to the present invention can be produced in accordance with the method traditionally being used in the art for producing an emulsion. More specifically, the oil-in-water emulsion composition can be produced by preparing an oil phase component and a water phase component separately, and mixing and emulsifying the water phase and the oil phase by means of a disperser or a homogenizer.

Examples

The present invention will be more specifically described below by way of Examples; however, the present invention is not limited by these Examples. Unless otherwise specified, the units of the contents are mass %. Prior to describing Examples, the evaluation methods employed in the present invention will be described.

(1) Non-Stickiness

Onto upper arms of 20 female panelists, a test sample was applied by hand. After the application, stickiness was evaluated in the form of a questionnaire and determined based on the following criteria:

⊚: The number of panelists answering that they felt neither stickiness nor slime was 16 or more.

○: The number of panelists answering that they felt neither stickiness nor slime was 12 to 15.

⊡: The number of panelists answering that they felt neither stickiness nor slime was 8 to 11.

x: The number of panelists answering that they felt neither stickiness nor slime was 7 or less.

(2) Firmness/Elasticity

Onto the upper arms of 20 female panelists, a test sample was applied by hand. Firmness/elasticity of the applied skin was evaluated in the form of a questionnaire and determined based on the following criteria:

⊚: The number of panelists answering that they felt firmness/elasticity of the applied skin was 16 or more.

○: The number of panelists answering that they felt firmness/elasticity of the applied skin was 12 to 15.

⊡: The number of panelists answering that they felt firmness/elasticity of the applied skin was 8 to 11.

x: The number of panelists answering that they felt firmness/elasticity of the applied skin was 7 or less.

(3) Roughness-Covering Effect Immediately after Application

Onto the upper arms of 20 female panelists, a test sample was applied by hand. A roughness-covering effect immediately after application was evaluated in the form of a questionnaire and determined based on the following criteria:

⊚: The number of panelists answering that they felt a roughness-covering effect on the applied skin immediately after application was 16 or more.

○: The number of panelists answering that they felt a roughness-covering effect on the applied skin immediately after application was 12 to 15.

⊡: The number of panelists answering that they felt a roughness-covering effect on the applied skin immediately after application was 8 to 11.

x: The number of panelists answering that they felt a roughness-covering effect on the applied skin immediately after application was 7 or less.

(4) Persistency of Roughness-Covering Effect

Onto the upper arms of 20 female panelists, a test sample was applied by hand. Persistency of roughness-covering effect was evaluated in the form of a questionnaire and determined based on the following criteria:

⊚: The number of panelists answering that the roughness-covering effect lasted on the applied skin was 16 or more.

○: The number of panelists answering that the roughness-covering effect lasted on the applied skin was 12 to 15.

⊡: The number of panelists answering that the roughness-covering effect lasted on the applied skin was 8 to 11.

x: The number of panelists answering that the roughness-covering effect lasted on the applied skin was 7 or less.

(5) Smoothness

Onto the upper arms of 20 female panelists, a test sample was applied by hand. Smoothness of the applied skin was evaluated in the form of a questionnaire and determined based on the following criteria:

⊚: The number of panelists answering that they felt smoothness of the applied skin was 16 or more.

○: The number of panelists answering that they felt smoothness of the applied skin was 12 to 15.

⊡: The number of panelists answering that they felt smoothness of the applied skin was 8 to 11.

x: The number of panelists answering that they felt smoothness of the applied skin was 7 or less.

(6) Moist Feeling

Onto the upper arms of 20 female panelists, a test sample was applied by hand. Moist feeling of the applied skin was evaluated in the form of a questionnaire and determined based on the following criteria:

⊚: The number of panelists answering that they experienced moist feeling of the applied skin was 16 or more.

○: The number of panelists answering that they experienced moist feeling of the applied skin was 12 to 15.

⊡: The number of panelists answering that they experienced moist feeling of the applied skin was 8 to 11.

x: The number of panelists answering that they experienced moist feeling of the applied skin was 7 or less.

(7) Shiny Appearance after Application

Onto the upper arms of 20 female panelists, a test sample was applied by hand. Shiny appearance of the applied skin was evaluated in the form of a questionnaire and determined based on the following criteria:

⊚: The number of panelists answering that they felt shiny appearance of the applied skin was 16 or more.

○: The number of panelists answering that they felt shiny appearance of the applied skin was 12 to 15.

⊡: The number of panelists answering that they felt shiny appearance of the applied skin was 8 to 11.

x: The number of panelists answering that they felt shiny appearance of the applied skin was 7 or less.

(8) Dispersibility of (A) Non-Emulsifying Crosslinked Polymethylsiloxane at the Time of Manufacturing Dispersibility was evaluated by visually observing the state of a test sample immediately after manufacturing and determined based on the following criteria:

○: Non-emulsifying crosslinked polymethylsiloxane is uniformly dispersed.

⊡: Non-emulsifying crosslinked polymethylsiloxane is slightly not dispersed.

x: Non-emulsifying crosslinked polymethylsiloxane is not dispersed.

(9) Aggregation of (A) Non-Emulsifying Crosslinked Polymethylsiloxane with Time

Test samples were allowed to stand still at 50° C. for 4 weeks and returned to room temperature. An aggregation state was evaluated by visual observation and determined based on the following criteria.

○: Abnormality is not observed.

⊡: Aggregation of non-emulsifying crosslinked polymethylsiloxane is slightly observed.

x: Aggregation of non-emulsifying crosslinked polymethylsiloxane is observed.

(10) Stability Over Time

Test samples were allowed to stand still at 50° C. for 4 weeks and returned to room temperature. Stability was evaluated by visual observation and determined based on the following criteria.

○: Abnormality is not observed.

⊡: Slight separation is observed.

x: Separation is observed.

<Evaluation on Content of (A) Non-Emulsifying Crosslinked Polymethylsiloxane>

Oil-in-water emulsion compositions (test samples) were prepared in accordance with the formulations shown in the following Table 1 and individual properties were evaluated in accordance with the above evaluation methods. The results are also shown in Table 1.

TABLE 1

| Composition | | Component | Comparative Example 1 | Comparative Example 2 | Comparative Example 3 | Comparative Example 4 | Comparative Example 5 |
|---|---|---|---|---|---|---|---|
| (1) | E | Water | 60.95 | 55.95 | 45.95 | 25.95 | 45.95 |
| (2) | | Glycerin | 10 | 10 | 10 | 10 | 10 |
| (3) | | 1,3-butylene glycol | 8.4 | 8.4 | 8.4 | 8.4 | 8.4 |
| (4) | | Dipropylene glycol | 5 | 5 | 5 | 5 | 5 |
| (5) | C | PEG-9 polydimethylsiloxyethyldimethicone | 1 | 1 | 1 | 1 | 1 |
| (6) | D | Dimethicone | 8 | 8 | 8 | 8 | 8 |
| (7) | D | Diphenylsiloxyphenyltrimethicone | 1 | 1 | 1 | 1 | 1 |
| (8) | a1 | Mixture of dimethicone cross polymer/dimethicone 5 mPa·s (crosslinked polymer: 16%) | 0 | 5 (0.8) | 15 (2.4) | 35 (5.6) | 14 (2.24) |
| (9) | a2 | Mixture of a (dimethicone/phenylvinyldimethicone) cross polymer/phenyltrimethicone (crosslinked polymer: 15%) | 0 | 0 | 0 | 0 | 1 (0.15) |
| (10) | B | (PEG-240/decyltetradeceth-20/HDI) copolymer | 1.6 | 1.6 | 1.6 | 1.6 | 1.6 |
| (11) | | Carbomer | 0.12 | 0.12 | 0.12 | 0.12 | 0.12 |
| (12) | | EDTA-2Na | 0.07 | 0.07 | 0.07 | 0.07 | 0.07 |
| (13) | | Sodium citrate | 0.24 | 0.24 | 0.24 | 0.24 | 0.24 |
| (14) | | Citric acid | 0.06 | 0.06 | 0.06 | 0.06 | 0.06 |
| (15) | | Potassium hydroxide | 0.04 | 0.04 | 0.04 | 0.04 | 0.04 |
| (16) | | Talc | 3 | 3 | 3 | 3 | 3 |
| (17) | | Phenoxyethanol | 0.5 | 0.5 | 0.5 | 0.5 | 0.5 |
| (18) | | Fragrance | 0.02 | 0.02 | 0.02 | 0.02 | 0.02 |
| | | Total | 100 | 100 | 100 | 100 | 100 |
| | | Total amount of non-emulsifying crosslinked polymethylsiloxanes ((a1) + (a2)) (mass %) | 0 | 0.8 | 2.4 | 5.6 | 2.39 |
| | | Ratio of (a2)/(a1) | — | 0 | 0 | 0 | 0.07 |

| Evaluation | Item | | | | | |
|---|---|---|---|---|---|---|
| | roughness-covering effect immediately after application | X | ○ | ◎ | ◎ | ◎ |
| | Persistency of roughness-covering effect | X | X | ○ | ○ | ○ |
| | Smoothness | X | ○ | ◎ | ◎ | ◎ |
| | Moist feeling | X | ○ | ○ | ○ | ○ |
| | Shiny appearance after application | X | ○ | ○ | ○ | ○ |
| | Non-stickiness | ○ | ○ | ○ | X | ○ |

| Composition | | Component | Example 1 | Example 2 | Comparative Example 6 | Comparative Example 7 |
|---|---|---|---|---|---|---|
| (1) | E | Water | 45.95 | 45.95 | 45.95 | 45.95 |
| (2) | | Glycerin | 10 | 10 | 10 | 10 |
| (3) | | 1,3-butylene glycol | 8.4 | 8.4 | 8.4 | 8.4 |
| (4) | | Dipropylene glycol | 5 | 5 | 5 | 5 |
| (5) | C | PEG-9 polydimethylsiloxyethyldimethicone | 1 | 1 | 1 | 1 |
| (6) | D | Dimethicone | 8 | 8 | 8 | 8 |
| (7) | D | Diphenylsiloxyphenyltrimethicone | 1 | 1 | 1 | 1 |
| (8) | a1 | Mixture of dimethicone cross polymer/dimethicone 5 mPa·s (crosslinked polymer: 16%) | 10 (1.6) | 5 (0.8) | 1 (0.16) | 0 |
| (9) | a2 | Mixture of a (dimethicone/phenylvinyldimethicone) cross polymer/phenyltrimethicone (crosslinked polymer: 15%) | 5 (0.75) | 10 (1.5) | 14 (2.1) | 15 (2.25) |
| (10) | B | (PEG-240/decyltetradeceth-20/HDI) copolymer | 1.6 | 1.6 | 1.6 | 1.6 |
| (11) | | Carbomer | 0.12 | 0.12 | 0.12 | 0.12 |
| (12) | | EDTA-2Na | 0.07 | 0.07 | 0.07 | 0.07 |
| (13) | | Sodium citrate | 0.24 | 0.24 | 0.24 | 0.24 |
| (14) | | Citric acid | 0.06 | 0.06 | 0.06 | 0.06 |
| (15) | | Potassium hydroxide | 0.04 | 0.04 | 0.04 | 0.04 |
| (16) | | Talc | 3 | 3 | 3 | 3 |
| (17) | | Phenoxyethanol | 0.5 | 0.5 | 0.5 | 0.5 |
| (18) | | Fragrance | 0.02 | 0.02 | 0.02 | 0.02 |
| | | Total | 100 | 100 | 100 | 100 |
| | | Total amount of non-emulsifying crosslinked polymethylsiloxanes ((a1) + (a2)) (mass %) | 2.35 | 2.3 | 2.26 | 2.25 |
| | | Ratio of (a2)/(a1) | 0.47 | 1.89 | 13.1 | — |

| Evaluation | Item | | | | |
|---|---|---|---|---|---|
| | roughness-covering effect immediately after application | ◎ | ○ | ○ | ○ |

TABLE 1-continued

| | | | | |
|---|---|---|---|---|
| Persistency of roughness-covering effect | ○ | ◎ | ⊠ | ⊠ |
| Smoothness | ◎ | ○ | ⊠ | ⊠ |
| Moist feeling | ○ | ◎ | ◎ | ◎ |
| Shiny appearance after application | ○ | ◎ | ◎ | ◎ |
| Non-stickiness | ◎ | ○ | ○ | ○ |

In Table 1, the following products were used as A (a1, a2), B, C components.
(5) C component: "KF-6028" (trade name) manufactured by Shin-Etsu Chemical Co., Ltd.
(8) a1 component: "DC9041" (trade name) manufactured by Dow Corning Toray Co., Ltd.
(9) a2 component: "KSG-18" (trade name) manufactured by Shin-Etsu Chemical Co., Ltd.
(10) B component: "ADEKA NOL GT-700" (trade name) manufactured by ADEKA Corporation.

In the columns of component a1 and a2, the content of the product is shown and the actual quantity of a crosslinked polymer contained in the product is shown within parentheses.

As is apparent from Table 1, in the cases (Comparative Examples 1 to 4 and 7) where none or only one of the two types (a1, a2) of (A) non-emulsifying crosslinked polymethylsiloxanes is contained and in the cases (Comparative Examples 5 and 6) where the mass ratio ((a2)/(a1)) is outside the range of 0.1 to 2.5 even if both of these are contained, the roughness-covering effect and/or its persistency were insufficient. In contrast, in the cases (Examples 1 and 2) where these components are contained such that the mass ratio ((a2)/(a1)) falls within the range of 0.1 to 2.5, the roughness-covering effect and its persistency were sufficiently obtained; at the same time, satisfactory results were obtained with respect to sense of use including smoothness, moist feeling, shiny appearance after application and non-stickiness.

<Evaluation on Content of (C) Polyether-Modified Silicone>

Oil-in-water emulsion compositions (test samples) were prepared in accordance with the formulations shown in the following Table 2 and individual properties were evaluated in accordance with the above evaluation methods. The results are also shown in Table 2.

TABLE 2

| Composition | | Component | Comparative Example 8 | Comparative Example 9 | Example 1 | Example 3 | Comparative Example 10 |
|---|---|---|---|---|---|---|---|
| (1) | E | Water | 46.95 | 46.65 | 45.95 | 41.95 | 39.95 |
| (2) | | Glycerin | 10 | 10 | 10 | 10 | 10 |
| (3) | | 1,3-butylene glycol | 8.4 | 8.4 | 8.4 | 8.4 | 8.4 |
| (4) | | Dipropylene glycol | 5 | 5 | 5 | 5 | 5 |
| (5) | C | PEG-9 polydimethyl-siloxyethyldimethicone | 0 | 0.3 | 1 | 5 | 7 |
| (6) | D | Dimethicone | 8 | 8 | 8 | 8 | 8 |
| (7) | D | Diphenylsiloxy-phenyltrimethicone | 1 | 1 | 1 | 1 | 1 |
| (8) | a1 | Mixture of dimethicone cross polymer/dimethicone 5 mPa·s (crosslinked polymer: 16%) | 10 (1.6) | 10 (1.6) | 10 (1.6) | 10 (1.6) | 10 (1.6) |
| (9) | a2 | Mixture of a (dimethicone/phenylvinyldimethicone) cross polymer/phenyltrimethicone (crosslinked polymer: about 15%) | 5 (0.75) | 5 (0.75) | 5 (0.75) | 5 (0.75) | 5 (0.75) |
| (10) | B | (PEG-240/decyltetradeceth-20/HDI) copolymer | 1.6 | 1.6 | 1.6 | 1.6 | 1.6 |
| (11) | | Carbomer | 0.12 | 0.12 | 0.12 | 0.12 | 0.12 |
| (12) | | EDTA-2Na | 0.07 | 0.07 | 0.07 | 0.07 | 0.07 |
| (13) | | Sodium citrate | 0.24 | 0.24 | 0.24 | 0.24 | 0.24 |
| (14) | | Citric acid | 0.06 | 0.06 | 0.06 | 0.06 | 0.06 |
| (15) | | Potassium hydroxide | 0.04 | 0.04 | 0.04 | 0.04 | 0.04 |
| (16) | | Talc | 3 | 3 | 3 | 3 | 3 |
| (17) | | Phenoxyethanol | 0.5 | 0.5 | 0.5 | 0.5 | 0.5 |
| (18) | | Fragrance | 0.02 | 0.02 | 0.02 | 0.02 | 0.02 |
| | | Total | 100 | 100 | 100 | 100 | 100 |
| Evaluation | | Item | | | | | |
| | | Productivity (dispersibility of (A) non-emulsifying crosslinked polymethylsiloxane at the time of manufacturing) | X | X | ○ | ○ | ○ |

TABLE 2-continued

| Composition | Component | Comparative Example 8 | Comparative Example 9 | Example 1 | Example 3 | Comparative Example 10 |
|---|---|---|---|---|---|---|
| | Aggregation of (A) non-emulsifying crosslinked polymethylsiloxane with time | X | X | ○ | ○ | ○ |
| | Non-stickiness | ◎ | ◎ | ◎ | ○ | X |

In Table 2, the following products were used as A (a1, a2), B, C components.
(5) C component: "KF-6028" (trade name) manufactured by Shin-Etsu Chemical Co., Ltd.
(8) a1 component: "DC9041" (trade name) manufactured by Dow Corning Toray Co., Ltd.
(9) a2 component: "KSG-18" (trade name) manufactured by Shin-Etsu Chemical Co., Ltd.
(10) B component: "ADEKA NOL GT-700" (trade name) manufactured by ADEKA Corporation.

In the columns of component a1 and a2, the content of the product is shown and the actual quantity of a crosslinked polymer contained in the product is shown within parentheses.

As is apparent from Table 2, in the cases (Comparative Examples 8 and 9) where the content of (C) a polyether-modified silicone is less than 0.5 mass %, the dispersibility of (A) a non-emulsifying crosslinked polymethylsiloxane at the time of manufacturing was poor and aggregation of (A) the non-emulsifying crosslinked polymethylsiloxane with time was observed. Furthermore, in the case (Comparative Example 10) where the content of (C) a polyether-modified silicone exceeds 5.0 mass %, the composition became sticky. In contrast, in the cases (Examples 1 and 3) where (C) a polyether-modified silicone was contained within the range of 0.5 to 5.0 mass %, dispersibility of (A) a non-emulsifying crosslinked polymethylsiloxane at the time of manufacturing was satisfactory and aggregation with time was suppressed and sense of use was satisfactory without stickiness.

<Evaluation on Content of (B) Associative Thickening Agent>

Oil-in-water emulsion compositions (test samples) were prepared in accordance with the formulations shown in the following Table 3 and individual properties were evaluated in accordance with the above evaluation methods. The results are also shown in Table 3.

TABLE 3

| | | Component | Comparative Example 11 | Comparative Example 12 | Example 4 | Example 5 | Comparative Example 13 |
|---|---|---|---|---|---|---|---|
| (1) | E | Water | 47.55 | 47.25 | 46.55 | 42.55 | 37.55 |
| (2) | | Glycerin | 10 | 10 | 10 | 10 | 10 |
| (3) | | 1,3-butylene glycol | 8.4 | 8.4 | 8.4 | 8.4 | 8.4 |
| (4) | | Dipropylene glycol | 5 | 5 | 5 | 5 | 5 |
| (5) | C | PEG-9 polydimethyl-siloxyethyldimethicone | 1 | 1 | 1 | 1 | 1 |
| (6) | D | Dimethicone | 8 | 8 | 8 | 8 | 8 |
| (7) | D | Diphenylsiloxy-phenyltrimethicone | 1 | 1 | 1 | 1 | 1 |
| (8) | a1 | Mixture of dimethicone cross polymer/dimethicone 5 mPa·s (crosslinked polymer: 16%) | 10 (1.6) | 10 (1.6) | 10 (1.6) | 10 (1.6) | 10 (1.6) |
| (9) | a2 | Mixture of a (dimethicone/phenylvinyldimethicone) cross polymer/phenyltrimethicone (crosslinked polymer: about 15%) | 5 (0.75) | 5 (0.75) | 5 (0.75) | 5 (0.75) | 5 (0.75) |
| (10) | B | (PEG-240/decyltetradeceth-20/HDI) copolymer | 0 | 0.3 | 1 | 5 | 10 |
| (11) | | Carbomer | 0.12 | 0.12 | 0.12 | 0.12 | 0.12 |
| (12) | | EDTA-2Na | 0.07 | 0.07 | 0.07 | 0.07 | 0.07 |
| (13) | | Sodium citrate | 0.24 | 0.24 | 0.24 | 0.24 | 0.24 |
| (14) | | Citric acid | 0.06 | 0.06 | 0.06 | 0.06 | 0.06 |
| (15) | | Potassium hydroxide | 0.04 | 0.04 | 0.04 | 0.04 | 0.04 |
| (16) | | Talc | 3 | 3 | 3 | 3 | 3 |
| (17) | | Phenoxyethanol | 0.5 | 0.5 | 0.5 | 0.5 | 0.5 |
| (18) | | Fragrance | 0.02 | 0.02 | 0.02 | 0.02 | 0.02 |
| | | Total | 100 | 100 | 100 | 100 | 100 |
| Evaluation | | Item | | | | | |
| | | Viscosity (mPa·s) | 1000 or less | 1000 or less | 17000 | 80000 | 250000 or more |
| | | Stability over time | X | X | ○ | ○ | ○ |
| | | Firmness/elasticity | X | X | ◎ | ◎ | ◎ |
| | | Non-stickiness | ◎ | ◎ | ◎ | ○ | X |

In Table 3, the following products were used as A (a1, a2), B, C components.
(5) C component: "KF-6028" (trade name) manufactured by Shin-Etsu Chemical Co., Ltd.
(8) a1 component: "DC9041" (trade name) manufactured by Dow Corning Toray Co., Ltd.
(9) a2 component: "KSG-18" (trade name) manufactured by Shin-Etsu Chemical Co., Ltd.
(10) B component: "ADEKA NOL GT-700" (trade name) manufactured by ADEKA Corporation.

In the columns of component a1 and a2, the content of the product is shown and the actual quantity of a crosslinked polymer contained in the product is shown within parentheses.

As is apparent from Table 3, in the cases (Comparative Examples 11 and 12) where the content of (B) an associative thickening agent was less than 0.5 mass %, viscosity was low, stability over time was poor and no firmness/elasticity was felt. Furthermore, in the case (Comparative Example 13) where the content of (B) an associative thickening agent exceeded 5.0 mass %, the resultant composition became sticky. In contrast, in the cases (Examples 4 and 5) where the content of (B) an associative thickening agent fell within the range of 0.5 to 5.0 mass %, the composition had appropriate viscosity and excellent stability over time and provided firmness/elasticity and satisfactory sense of use without stickiness.

<Comparison with Cosmetics Containing Silica-Coated Silicone Elastomer>

Oil-in-water emulsion compositions (test samples) were prepared in accordance with the formulations shown in the following Table 4 and individual properties were evaluated in accordance with the above evaluation methods. The results are also shown in Table 4.

TABLE 4

| | | Component | Comparative Example 14 | Comparative Example 15 | Comparative Example 16 | Comparative Example 17 | Example 1 | Example 2 |
|---|---|---|---|---|---|---|---|---|
| (1) | E | Water | 72.25 | 59.25 | 80.25 | 73.25 | 45.95 | 45.95 |
| (2) | | Glycerin | 7 | 7 | 3 | 10 | 10 | 10 |
| (3) | | 1,3-butylene glycol | 7 | 7 | 7 | 7 | 8.4 | 8.4 |
| (4) | | Dipropylene glycol | 0 | 0 | 0 | 0 | 5 | 5 |
| (5) | C | PEG-9 polydimethylsiloxyethyldimethicone | 0 | 0 | 0 | 0 | 1 | 1 |
| (6) | C | PEG-10 Dimethicone | 0 | 0 | 0 | 0 | 0 | 0 |
| (7) | D | Dimethicone | 0 | 0 | 0 | 0 | 8 | 8 |
| (8) | D | Diphenylsiloxyphenyltrimethicone | 0 | 0 | 0 | 0 | 1 | 1 |
| (9) | D | Cyclomethicone | 0 | 0 | 0 | 0 | 0 | 0 |
| (10) | a1 | Mixture of dimethicone cross polymer/dimethicone 5 mPa·s (crosslinked polymer: 16%) | 0 | 0 | 0 | 0 | 10 (1.6) | 5 (0.8) |
| (11) | a2 | Mixture of a (dimethicone/phenylvinyldimethicone) cross polymer/phenyltrimethicone (crosslinked polymer: about 15%) | 0 | 0 | 0 | 0 | 5 (0.75) | 10 (1.5) |
| (12) | a2 | Mixture of polysilicone-11/dimethicone 6 mPa·s (crosslinked polymer: about 18%) | 0 | 0 | 0 | 0 | 0 | 0 |
| (13) | a2 | Mixture of (vinyldimethicone/lauryldimethicone) cross polymer/liquid paraffin (crosslinked polymer: about 30%) | 0 | 0 | 0 | 0 | 0 | 0 |
| (14) | a2 | (Dimethicone/vinyldimethicone) cross polymer (coated with silica) | 7 | 20 | 3 | 3 | 0 | 0 |
| (15) | B | (PEG-240(decyltetradeceth-20/HDI) copolymer | 2 | 2 | 2 | 2 | 1.6 | 1.6 |
| (16) | | Succinoglycan | 0.15 | 0.15 | 0.15 | 0.15 | 0 | 0 |
| (17) | | Carbomer | 0 | 0 | 0 | 0 | 0.12 | 0.12 |
| (18) | | Xanthan gum | 0 | 0 | 0 | 0 | 0 | 0 |
| (19) | | EDTA-2Na | 0.1 | 0.1 | 0.1 | 0.1 | 0.07 | 0.07 |
| (20) | | Sodium citrate | 0.08 | 0.08 | 0.08 | 0.08 | 0.24 | 0.24 |
| (21) | | Citric acid | 0.02 | 0.02 | 0.02 | 0.02 | 0.06 | 0.06 |
| (22) | | Potassium hydroxide | 0 | 0 | 0 | 0 | 0.04 | 0.04 |
| (23) | | Talc | 0 | 0 | 0 | 0 | 3 | 3 |
| (24) | | Mica | 0 | 0 | 0 | 0 | 0 | 0 |
| (25) | | Phenoxyethanol | 0.4 | 0.4 | 0.4 | 0.4 | 0.5 | 0.5 |
| (26) | | Fragrance | 0 | 0 | 0 | 0 | 0.02 | 0.02 |
| (27) | | Ethanol | 4 | 4 | 4 | 4 | 0 | 0 |
| | | Total | 100 | 106 | 100 | 100 | 100 | 100 |
| | | Ratio of (a2)/(a1) | — | — | — | — | 0.47 | 1.89 |
| Evatuation | | Item | | | | | | |
| | | Viscosity (mPa·s) | — | — | — | — | 25000 | 24000 |
| | | Stability over time | ◯ | ◯ | ◯ | ◯ | ◯ | ◯ |
| | | Firmness/elasticity | ◉ | ◉ | ◉ | ◉ | ◉ | ◉ |
| | | Non-stickiness | ⌧ | ⌧ | ◯ | ◯ | ◉ | ◯ |
| | | Productivity (dispersibility of (A) non-emulsifying crosslinked polymethylsiloxane at the time of manufacturing) | — | — | — | — | ◯ | ◯ |
| | | Aggregation of (A) non-emulsifying crosslinked polymethylsiloxane with time | — | — | — | — | ◯ | ◯ |
| | | roughness-covering effect immediately after application | ◯ | ◯ | ◯ | ◯ | ◉ | ◯ |

TABLE 4-continued

| | | |
|---|---|---|
| Persistency of roughness-covering effect | ◎ ◎ ◎ ◎ | ○ ◎ |
| Smoothness | ◎ ◎ ◎ ◎ | ◎ ○ |
| Moist feeling | ○ ○ ◎ ○ | ○ ◎ |
| Shiny appearance after application | ◎ ◎ ◎ ◎ | ○ ◎ |

| | | Component | Example 3 | Example 4 | Example 5 | Example 6 | Example 7 | Example 8 |
|---|---|---|---|---|---|---|---|---|
| (1) | E | Water | 41.95 | 46.55 | 42.55 | 48.07 | 48.07 | 43.95 |
| (2) | | Glycerin | 10 | 10 | 10 | 10 | 10 | 10 |
| (3) | | 1,3-butylene glycol | 8.4 | 8.4 | 8.4 | 8.4 | 8.4 | 8.4 |
| (4) | | Dipropylene glycol | 5 | 5 | 5 | 5 | 5 | 5 |
| (5) | C | PEG-9 polydimethylsiloxyethyldimethicone | 5 | 1 | 1 | 1 | 1 | 0 |
| (6) | C | PEG-10 Dimethicone | 0 | 0 | 0 | 0 | 0 | 1 |
| (7) | D | Dimethicone | 8 | 8 | 8 | 0 | 0 | 8 |
| (8) | D | Diphenylsiloxyphenyltrimethicone | 1 | 1 | 1 | 10 | 10 | 0 |
| (9) | D | Cyclomethicone | 0 | 0 | 0 | 0 | 0 | 3 |
| (10) | a1 | Mixture of dimethicone cross polymer/dimethicone 5 mPa·s (crosslinked polymer: 16%) | 10 (1.6) | 10 (1.6) | 10 (1.6) | 10 (1.6) | 10 (1.6) | 5 (0.8) |
| (11) | a2 | Mixture of a (dimethicone/phenylvinyldimethicone) cross polymer/phenyltrimethicone (crosslinked polymer: about 15%) | 5 (0.75) | 5 (0.75) | 5 (0.75) | 0 | 0 | 5 (0.75) |
| (12) | a2 | Mixture of polysilicone-11/dimethicone 6 mPa·s (crosslinked polymer: about 18%) | 0 | 0 | 0 | 5 (0.9) | 0 | 5 (0.9) |
| (13) | a2 | Mixture of (vinyldimethicone/lauryldimethicone) cross polymer/liquid paraffin (crosslinked polymer: about 30%) | 0 | 0 | 0 | 0 | 5 (1.5) | 0 |
| (14) | a2 | (Dimethicone/vinyldimethicone) cross polymer (coated with silica) | 0 | 0 | 0 | 0 | 0 | 0 |
| (15) | B | (PEG-240(decyltetradeceth-20/HDI) copolymer | 1.6 | 1 | 5 | 1.4 | 1.4 | 1.6 |
| (16) | | Succinoglycan | 0 | 0 | 0 | 0 | 0 | 0 |
| (17) | | Carbomer | 0.12 | 0.12 | 0.12 | 0 | 0 | 0.12 |
| (18) | | Xanthan gum | 0 | 0 | 0 | 0.2 | 0.2 | 0 |
| (19) | | EDTA-2Na | 007 | 0.07 | 0.07 | 0.07 | 0.07 | 0.07 |
| (20) | | Sodium citrate | 0.24 | 0.24 | 0.24 | 0.24 | 0.24 | 0.24 |
| (21) | | Citric acid | 0.06 | 0.06 | 0.06 | 0.06 | 0.06 | 0.06 |
| (22) | | Potassium hydroxide | 0.04 | 0.04 | 0.04 | 0.04 | 0.04 | 0.04 |
| (23) | | Talc | 3 | 3 | 3 | 0 | 0 | 0 |
| (24) | | Mica | 0 | 0 | 0 | 0 | 0 | 3 |
| (25) | | Phenoxyethanol | 0.5 | 0.5 | 0.5 | 0.5 | 0.5 | 0.5 |
| (26) | | Fragrance | 0.02 | 0.02 | 0.02 | 0.02 | 0.02 | 0.02 |
| (27) | | Ethanol | 0 | 0 | 0 | 0 | 0 | 0 |
| | | Total | 100 | 100 | 100 | 100 | 100 | 100 |
| | | Ratio of (a2)/(a1) | 0.47 | 0.47 | 0.47 | 0.56 | 0.94 | 2.1 |

| Evatuation | Item | | | | | | |
|---|---|---|---|---|---|---|---|
| | Viscosity (mPa·s) | 22000 | 17000 | 80000 | 20000 | 29000 | 24500 |
| | Stability over time | ○ | ○ | ○ | ○ | ○ | ○ |
| | Firmness/elasticity | ◎ | ◎ | ◎ | ◎ | ◎ | ◎ |
| | Non-stickiness | ○ | ◎ | ○ | ○ | ○ | ○ |
| | Productivity (dispersibility of (A) non-emulsifying crosslinked polymethylsiloxane at the time of manufacturing) | ○ | ○ | ○ | ○ | ○ | ○ |
| | Aggregation of (A) non-emulsifying crosslinked polymethylsiloxane with time | ○ | ○ | ○ | ○ | ○ | ○ |
| | roughness-covering effect immediately after application | ◎ | ◎ | ◎ | ◎ | ◎ | ○ |
| | Persistency of roughness-covering effect | ◎ | ◎ | ◎ | ◎ | ◎ | ◎ |
| | Smoothness | ◎ | ◎ | ◎ | ◎ | ◎ | ○ |
| | Moist feeling | ○ | ○ | ○ | ○ | ○ | ◎ |
| | Shiny appearance after application | ○ | ○ | ○ | ○ | ○ | ◎ |

In Table 4, the following products were used as A (a1, a2), B, C components and succinoglycan.

(5) C component: "KF-6028" (trade name) manufactured by Shin-Etsu Chemical Co., Ltd.

(6) C component: "KF-6017" (trade name) manufactured by Shin-Etsu Chemical Co., Ltd.

(10) a1 component: "DC9041" (trade name) manufactured by Dow Corning Toray Co., Ltd.

(11) a2 component: "KSG-18" (trade name) manufactured by Shin-Etsu Chemical Co., Ltd.

(12) a2 component: "GRANSIL DMG-6" (trade name) manufactured by GRANT.

(13) a2 component: "KSG-41" (trade name) manufactured by Shin-Etsu Chemical Co., Ltd.
(14) a2 component: "9701 COSMETIC POWDER" (trade name) manufactured by Dow Corning Toray Co., Ltd.
(15) B component: "ADEKA NOL GT-700" (trade name) manufactured by ADEKA Corporation.
(16) Succinoglycan (water-soluble thickening agent): "Rheozan SH" (trade name) manufactured by RHODIA.

Furthermore, in the columns of component a1 and a2, the content of the product is shown and the actual quantity of a crosslinked polymer contained in the product is shown within parentheses.

As is apparent from Table 4, in compositions (Comparative Examples 14 to 17) containing a silica-coated silicone elastomer but not containing (a1) a dimethicone cross polymer, (C) a polyether-modified silicone and (D) a silicone oil, and described in Patent document 1, roughness-covering effect and its persistency tended to deteriorate. This type of composition can overlay on a foundation for reapplying makeup due to the absence of an oil content; however sense of use such as smoothness, shiny appearance and moist feeling tended to deteriorate. In contrast, compositions (Examples 1 to 8) containing (A) a non-emulsifying crosslinked polymethylsiloxane, (B) an associative thickening agent, (C) a polyether-modified silicone, (D) a silicone oil and (E) water in a predetermined ratio showed excellent evaluation results with respect to either one of the roughness-covering effect and the sense of use.

FORMULATION EXAMPLE

Now, a formulation example of the oil-in-water emulsion composition of the present invention will be described below. The present invention, needless to say, is not particularly limited by the formulation example and specified by the claims. Note that the content is expressed by mass % relative to the total amount of the product.

Formulation Example 1

Gel Cream for Eyes

| (Name of component) | content (%) |
|---|---|
| (1) Water | 45.95 |
| (2) Glycerin | 10 |
| (3) 1,3-Butylene glycol | 8.4 |
| (4) Dipropylene glycol | 5 |
| (5) PEG-9 polydimethylsiloxyethyldimethicone | 1 |
| (6) Dimethicone | 8 |
| (7) Diphenylsiloxyphenyltrimethicone | 1 |
| (8) Mixture of dimethicone cross polymer/dimethicone 5 mPa · s (crosslinked polymer: 16%) | 10 |
| (9) Mixture of a (dimethicone/phenylvinyldimethicone) cross polymer/phenyltrimethicone (crosslinked polymer: about 15%) | 5 |
| (10) (PEG-240/decyltetradeceth-20/HDI) copolymer | 1.6 |
| (11) Carbomer | 0.12 |
| (12) EDTA-2Na | 0.07 |
| (13) Sodium citrate | 0.24 |
| (14) Citric acid | 0.06 |
| (15) Potassium hydroxide | 0.04 |
| (16) Talc | 3 |
| (17) Phenoxy ethanol | 0.5 |
| (18) Flagrance | 0.02 |

[Process]

Components (1) to (4) and (11) to (15) were homogeneously mixed and dissolved/dispersed in an aqueous phase. To the aqueous phase, an oil phase, in which components (5) to (9), (17), and (18) were homogeneously dispersed, was gradually added and emulsified by a disper or a homogenizer. Subsequently, a component (16) was added, and a solution, which is prepared by dissolving a component (10) heated in a small amount of component (3), is added and homogeneously dispersed by a disper or a homogenizer.

The invention claimed is:

1. An oil-in-water emulsion composition comprising:
   (A) 0.5 to 5.0 mass % of a non-emulsifying crosslinked polymethylsiloxane comprising the following components (a1) and (a2):
      (a1) a dimethicone cross polymer, and
      (a2) a non-emulsifying crosslinked polymethylsiloxane except the dimethicone cross polymer,
   (B) 0.5 to 5.0 mass % of an associative thickening agent represented by the following general formula:

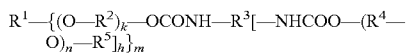

wherein $R^1$, $R^2$ and $R^4$ may be the same or different and represent a hydrocarbon group; $R^3$ represents a hydrocarbon group that may have a urethane bond; $R^5$ represents a linear or branched divalent hydrocarbon group; m is an integer of 2 or more; h is an integer of 1 or more; and k and n are each independently an integer of 0 to 1000,
   (C) 0.5 to 5.0 mass % of an agent for enhancing dispersion and inhibiting aggregation of said component (A), consisting of a polyether-modified silicone,
   (D) a silicone oil, and
   (E) water,
wherein the mass ratio ((a2)/(a1)) of the non-emulsifying crosslinked polymethylsiloxane (a2) except the dimethicone cross polymer relative to the dimethicone cross polymer (a1) falls within the range of 0.1 to 2.5.

2. The oil-in-water emulsion composition according to claim 1, wherein: the mass ratio ((a2)/(a1)) of the non-emulsifying crosslinked polymethylsiloxane (a2) except the dimethicone cross polymer relative to the dimethicone cross polymer (a1) falls within the range of 0.1 to 1.5.

3. The oil-in-water emulsion composition according to claim 1, wherein: the non-emulsifying crosslinked polymethylsiloxane (a2) except the dimethicone cross polymer is one or more selected from the group consisting of a dimethicone/vinyldimethicone cross polymer, a dimethicone/phenylvinyldimethicone cross polymer and a vinyldimethicone/lauryldimethicone cross polymer.

4. The oil-in-water emulsion composition according to claim 1, wherein: the content of the silicone oil is 3.0 to 30 mass % in the entire composition.

5. The oil-in-water emulsion composition according to claim 2, wherein: the non-emulsifying crosslinked polymethylsiloxane (a2) except the dimethicone cross polymer is one or more selected from the group consisting of a dimethicone/vinyldimethicone cross polymer, a dimethicone/phenylvinyldimethicone cross polymer and a vinyldimethicone/lauryldimethicone cross polymer.

6. The oil-in-water emulsion composition according to claim 2, wherein: the content of the silicone oil is 3.0 to 30 mass % in the entire composition.

7. The oil-in-water emulsion composition according to claim 5, wherein: the content of the silicone oil is 3.0 to 30 mass % in the entire composition.

8. The oil-in-water emulsion composition according to claim 3, wherein: the content of the silicone oil is 3.0 to 30 mass % in the entire composition.

9. The oil-in-water emulsion composition according to claim 1, wherein: the polyether-modified silicone is at least one selected from PEG-9 polydimethylsiloxyethyldimethicone and PEG-10 dimethicone.

* * * * *